United States Patent [19]

Voges et al.

[11] 3,972,938

[45] Aug. 3, 1976

[54] MANUFACTURE OF HEXAMETHYLENE DIAMINE

[75] Inventors: Dieter Voges, Mannheim; Leopold Hupfer, Friedelsheim; Siegfried Winderl, Heidelberg-Wieblingen; Karl Wilhelm Leonhard, Bobenheim-Roxheim; Herwig Hoffmann, Frankenthal, all of Germany

[73] Assignee: BASF Aktiengesellschaft, Ludwigshafen (Rhine), Germany

[22] Filed: Mar. 11, 1974

[21] Appl. No.: 450,145

[30] Foreign Application Priority Data
Mar. 14, 1973 Germany............................ 2312591

[52] U.S. Cl. ........................ 260/583 K; 260/583 P
[51] Int. Cl.² ........................................ C07C 87/14
[58] Field of Search...................... 260/583 K, 583 P

[56] References Cited
UNITED STATES PATENTS

| | | | |
|---|---|---|---|
| 2,166,150 | 7/1939 | Howk | 260/583 K |
| 2,166,152 | 7/1939 | Howk | 260/583 K |
| 2,200,282 | 5/1940 | Lazier | 260/583 P X |
| 2,284,525 | 5/1942 | Larchar et al. | 260/583 K |
| 3,398,195 | 8/1968 | Williams | 260/583 P |
| 3,471,563 | 10/1969 | Brake | 260/583 K |
| 3,478,102 | 11/1969 | Bende et al. | 260/583 K |
| 3,488,390 | 1/1970 | Carss et al. | 260/583 K |
| 3,758,584 | 9/1973 | Bivens et al. | 260/583 K |
| 3,773,832 | 11/1973 | Brake | 260/583 K |
| 3,821,305 | 6/1974 | Bartalini et al. | 260/583 K |

*Primary Examiner*—Paul F. Shaver
*Attorney, Agent, or Firm*—Johnston, Keil, Thompson & Shurtleff

[57] ABSTRACT

A process for the catalytic hydrogenation of adiponitrile in the presence of ammonia, in which a portion of the reaction mixture is recycled and specific molar ratios of adiponitrile and ammonia are maintained.

5 Claims, No Drawings

MANUFACTURE OF HEXAMETHYLENE DIAMINE

This application discloses and claims subject matter described in German patent application No. P 23 12 591.9, filed Mar. 14, 1973, which is incorporated herein by reference.

This invention relates to a process for the continuous manufacture of 1,6-hexamethylene diamine by catalytic hydrogenation of adiponitrile in liquid phase.

German Pat. No. 870,264 describes the catalytic reduction of adiponitrile in liquid phase with hydrogen in the presence of ammonia and under pressure to form 1,6-hexamethylene diamine. Although the resulting reaction product is used as a diluent for the adiponitrile to be hydrogenated, the said process is unsatisfactory on account of the by-products which are formed.

It is an object of the invention to provide a continuous process for the manufacture of 1,6-hexamethylene diamine from adiponitrile, which process produces few by-products and requires a minimum amount of ammonia to give an easily controllable reaction. This object is achieved by the present invention.

The invention provides a process for the continuous manufacture of 1,6-hexamethylene diamine which comprises hydrogenating adiponitrile in the presence of ammonia in liquid phase and hydrogen and also in the presence of hydrogenation catalysts at a hydrogen partial pressure of from 20 to 300 atmospheres gage and at a temperature of from 40° to 130°C, in a reaction zone, and recycling to said reaction zone the major portion of the hydrogenated reaction mixture obtained downstream of the reaction zone, fresh adiponitrile and ammonia being added to the recycled hydrogenated reaction mixture in a molar ratio of from 1:10 to 1:15 and the amount of hydrogenated reaction mixture recycled being such that the overall molar ratio of adiponitrile to ammonia on entering the reaction zone is from 1:40 to 1:55.

Advantageously, the reaction zone is elongated and tubular. For example, a vertical tube has proved successful. Conveniently, the catalyst present in the reaction zone is used in the form of a simple packing. The catalysts used are advantageously cobalt compounds with or without the addition of manganese, chromium, silver and phosphoric acid. The catalysts are generally of the fixed-bed type in the form of pellets, spheres or tablets. They may be unsupported or they may be on carriers such as pumice, aluminum oxide or silicates, which may be impregnated with the catalysts in the form of salts, or the catalysts may be used in the form of their metal oxides and mixed and shaped with said supports. Advantageously, at least a portion of the metal oxides or salts is activated before the commencement of hydrogenation by effecting reduction thereof with hydrogen under usual conditions.

The process of the invention for the continuous hydrogenation of adiponitrile is generally carried out at pressures of from 20 to 300 and preferably from 30 to 260 atmospheres gage hydrogen partial pressure and generally at temperatures of from 40° to 130°C and preferably from 50° to 100°C, the total rate of liquid flow advantageously being from 30 to 55 $m^3/m^2/hr$ and the rate of gas flow advantageously being from 10 to 50 $m^3/m^2/hr$ (STP), based on the free cross-section of the reactor at the reaction zone.

As the reaction is very exothermic, the lower temperatures in the above ranges relate to the inlet end of the reaction zone and the higher temperatures to the outlet end thereof.

In the hydrogenation of adiponitrile it has been found necessary to carry out the process in the presence of ammonia in order to suppress the formation of undesirable by-products, particularly hexamethylene imine and higher condensates such as bis-hexamethylene triamine. It has also been found necessary, in order to avoid hot spots during the exothermic hydrogenation, to carry out the process using a diluent, the recycled hydrogenated reaction mixture serving this very purpose.

For example, the following procedure has proved successful. Use is made of a vertical tube packed with granular catalyst, and the hydrogenated reaction mixture is removed from the base thereof via a liquid separator. A minor portion is removed therefrom, freed from ammonia in the usual manner and then worked up. The major portion of the hydrogenated reaction mixture is recycled to the top of the reaction zone to form a loop. The hydrogen is also introduced at the top of the reaction zone. Fresh adiponitrile and fresh ammonia are fed to the circulating reaction mixture, both in liquid form and in the amounts stated. Appropriate cooling means are provided within the loop to cool the reaction mixture to be hydrogenated to the temperature required at the inlet of the reaction zone, taking into account the temperature of the freshly added adiponitrile and ammonia. It has been found advantageous to cause the liquid reaction mixture to pass downwardly over the catalyst in the manner of a trickling column. In general, the ratio, by volume, of the recycled hydrogenated reaction mixture to the hydrogenated reaction mixture withdrawn, per unit of time, is from about 8:1 to 10:1. When the process is operated continuously, the amount of fresh adiponitrile and ammonia added is naturally the same as the amount of hydrogenated reaction mixture removed, corrected for the slight change in volume which occurs during the reaction.

We have found that the continuous hydrogenation of adiponitrile gives best results only when the molar ratio of adiponitrile and ammonia in the fresh feedstock is from 1:10 to 1:15 and preferably from 1:11 to 1:13 and is from 1:40 to 1:55 and preferably from 1:40 to 1:50 at the inlet of the reaction zone. The recycled 1,6-hexamethylene diamine undergoes no undesirable side reactions. If less than the specified amount of ammonia is used, the formation of by-products such as cyclic hexamethylene imine and high-boiling material, particularly bis-hexamethylene triamine, increases exponentially. Any further increase in the amount of ammonia has no added advantage.

Using the above molar ratios of adiponitrile to ammonia, the adiponitrile is converted to 1,6-hexamethylene diamine virtually quantitatively. Although the formation of by-products is mainly suppressed by the presence of the ammonia, this is also due, to a certain extent, to the dilution of the adiponitrile, since this measure avoids local overheating at the catalyst (hot spots) and obviates all uncontrollable increase in the reaction temperatures. Our process makes it possible to operate with relatively small amounts of fresh ammonia, although the amount of ammonia available at the inlet of the reaction zone is high, as stated. Furthermore, the 1,6-hexamethylene diamine removed is mixed with only from 10 to 15 molar equivalents of ammonia, which facilitates working up.

A further important economic advantage is the good utilization of the catalyst activity due to optimum liquid distribution over the catalyst and the associated increase in throughput.

The 1,6-hexamethylene diamine may be used, as usual and for example after distillation, as a raw material for the manufacture of fibers.

In the following Examples the parts are by weight. The pressure quoted is the hydrogen partial pressure. The abbreviations have the following meanings: ADN denotes adiponitrile, HMI denotes hexamethylene imine, BHT denotes bis-hexamethylene triamine and cat. denotes catalyst.

EXAMPLE 1

Through a vertical tube packed with 1,300 kg of catalyst consisting of 91% of cobalt, 5% of manganese and 4% of phosphoric acid there are continuously passed, after reduction of the catalyst, adiponitrile and ammonia, mixed with 10 times the amount of hydrogenated reaction mixture, in the presence of hydrogen at a hydrogen partial pressure of 200 atmospheres gage and at an entry temperature of 50°C. The temperature rises to about 95°C in the direction of flow. Conversion is more than 99.9%. From the data below it can be seen that the comparative experiment is operated outside the molar ratio of ADN to ammonia claimed in the present invention, whilst experiment 1 is operated within said range. Under the conditions of the invention, the throughput is higher and the amount of byproducts formed is lower than the condensates in the comparative experiment.

| ADN throughput [kg/kg/hr] | Molar ratio of ADN to NH$_3$ | | HMI BHT in product [%] | |
|---|---|---|---|---|
| | in feedstock | at reactor inlet | | |
| Comp. Exp. 1 0.071 | 1:8 | 1:36 | 0.09 | 1.83 |
| Experiment 1 0.092 | 1:12.5 | 1:44 | 0.07 | 1.05 |

EXAMPLE 2

720 kg of the above catalyst are packed into a vertical tubular hydrogenation reactor and reduced therein. Adiponitrile is passed therethrough at a rate of 0.127 kg/kg of cat. per hour under a pressure of 250 atmospheres gage. The inlet temperature of the reactor is 70°C and this rises in the direction of flow to 90°C. Hydrogen is circulated therethrough. By varying the recycled liquid, the ratio of adiponitrile to ammonia upstream of the reactor is varied. Tests 2 and 3 are carried out under the conditions proposed by the present invention. The comparative experiment 2 shows that an increase in the amount of ammonia upstream of the reactor to more than that specified in the present invention gives no change in the amount of byproducts formed.

| | Molar ratio of ADN to NH$_3$ | | HMI BHT in product [%] | |
|---|---|---|---|---|
| | in feedstock | at reactor inlet | | |
| Experiment 2 | 1:12.5 | 1:44 | 0.11 | 0.90 |
| Experiment 3 | 1:12.5 | 1:50 | 0.09 | 0.70 |
| Comp. Exp. 2 | 1:12.5 | 1:75 | 0.09 | 0.70 |

EXAMPLE 3

Hydrogenation is carried out as described in Example 2 but at a rate of 0.086 kg of ADN per kg per hr at a pressure of 80 atmospheres gage. The ratio of adiponitrile to ammonia in the fresh feed is varied above and below the range claimed.

The results show that a smaller proportion of ammonia than that specified in the invention causes a considerable rise in the amount of byproducts formed, whilst an increase in the amount of ammonia over and above the specified range has no added advantage.

| | Molar ratio of ADN to NH$_3$ | | HMI BHT in product [%] | |
|---|---|---|---|---|
| | in feedstock | at reactor inlet | | |
| Experiment 3 | 1: 8 | 1:42 | 0.55 | 1.7 |
| Experiment 4 | 1:14 | 1:52 | 0.52 | 1.1 |
| Comp. Exp. 4 | 1:17 | 1:55 | 0.52 | 1.0 |

We claim:

1. A process for the continuous manufacture of 1,6-hexamethylene diamine which comprises continuously hydrogenating adiponitrile in the presence of ammonia in liquid phase and hydrogen and in the presence of hydrogenation catalysts at a hydrogen partial pressure of from 20 to 300 atmospheres gage and a temperature of from 40° to 130°C, in a reaction zone, and continuously withdrawing and recycling the major portion of the hydrogenated reaction mixture leaving the reaction zone, wherein adiponitrile and ammonia are added to the recycled hydrogenated reaction mixture in a molar ratio of from 1:10 to 1:15, the amount of hydrogenated reaction mixture recycled being such that the overall molar ratio of adiponitrile to ammonia on entering the reaction zone is from 1:40 to 1:55.

2. A process as claimed in claim 1, wherein the molar ratio of adiponitrile to ammonia in the fresh feed is from 1:11 to 1:13.

3. A process as claimed in claim 1, wherein the molar ratio of adiponitrile to ammonia on entering the reaction zone is from 1:40 to 1:50.

4. A process as claimed in claim 1, wherein the reaction is carried out at temperatures of from 50° to 100°C.

5. A process as claimed in claim 1, wherein the reaction is carried out at a hydrogen partial pressure of from 30 to 260 atmospheres gage.

* * * * *